(12) United States Patent
Nomura et al.

(10) Patent No.: US 8,454,995 B2
(45) Date of Patent: Jun. 4, 2013

(54) PERORAL TABLET FOR BOWEL CLEANSING

(75) Inventors: Masafumi Nomura, Chuo-ku (JP); Tetsuyuki Nishiyama, Chuo-ku (JP); Mari Ichikawa, Chuo-ku (JP); Kyoko Fukaya, Chuo-ku (JP)

(73) Assignee: Zeria Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/392,605

(22) PCT Filed: Aug. 27, 2010

(86) PCT No.: PCT/JP2010/005285
§ 371 (c)(1), (2), (4) Date: Feb. 27, 2012

(87) PCT Pub. No.: WO2011/024467
PCT Pub. Date: Mar. 3, 2011

(65) Prior Publication Data
US 2012/0164219 A1    Jun. 28, 2012

(30) Foreign Application Priority Data
Aug. 31, 2009   (JP) ................................. 2009-199254

(51) Int. Cl.
*A61K 9/20* (2006.01)
(52) U.S. Cl.
USPC .......................................... 424/464; 424/465
(58) Field of Classification Search
None
See application file for complete search history.

(56) References Cited

U.S. PATENT DOCUMENTS

| | | | |
|---|---|---|---|
| 4,704,285 A | 11/1987 | Alderman | |
| 4,792,452 A | 12/1988 | Howard et al. | |
| 5,594,030 A | 1/1997 | Conte et al. | |
| 5,858,403 A * | 1/1999 | Borody et al. | 424/456 |
| 6,261,601 B1 | 7/2001 | Talwar et al. | |
| 2004/0176463 A1* | 9/2004 | Licht et al. | 514/616 |
| 2005/0129781 A1 | 6/2005 | Skiendzielewski et al. | |

FOREIGN PATENT DOCUMENTS

| | | |
|---|---|---|
| JP | 7 258078 | 10/1995 |
| JP | 10 130142 | 5/1998 |
| JP | 2007 512336 | 5/2007 |
| WO | 2005/051361 | 9/2005 |

OTHER PUBLICATIONS

International Search Report Issued Nov. 2, 2010 in PCT/JP10/05285 Filed Aug. 27, 2010.
European Search Report issued Feb. 7, 2013 in European Patent Application No. 10811523.9.

* cited by examiner

*Primary Examiner* — Susan Tran
(74) *Attorney, Agent, or Firm* — Oblon, Spivak, McClelland, Maier & Neustadt, L.L.P.

(57) ABSTRACT

To provide a peroral tablet for bowel cleansing which leaves no remains in the intestinal tract after bowel cleansing, which exhibits a dissolution property equivalent to that of conventional sodium phosphate-containing tablets including crystalline cellulose, and which is a small-size agent readily taken by a subject.
The peroral tablet for bowel cleansing containing the following ingredients (A) and (B):
(A) 80 to 95 mass % of sodium phosphate, and
(B) (B1) 7 to 11 mass % of hydroxypropyl cellulose which has such a particle size that $\geq 99\%$ of the particles thereof pass through a mesh having an opening of 350 μm and whose 2-mass % aqueous solution has a viscosity of 2.0 to 10.0 mPa.s,
(B2) 5 to 13 mass % of hydroxypropyl cellulose which has such a particle size that $\geq 99\%$ of the particles thereof pass through a mesh having an opening of 150 μm and whose 2-mass % aqueous solution has a viscosity of 3.0 to 5.9 mPa.s, or
(B3) 7 to 11 mass % of hydroxypropyl cellulose which has such a particle size that $\geq 99\%$ of the particles thereof pass through a mesh having an opening of 150 μm and whose 2-mass % aqueous solution has a viscosity of 6.0 to 4,000 mPa.s, and
having a water-insoluble ingredient content of 5 mass % or less.

9 Claims, No Drawings

PERORAL TABLET FOR BOWEL CLEANSING

TECHNICAL FIELD

The present invention relates to a peroral bowel-cleansing agent which serves as a preliminary treatment employed before colonoscopy.

BACKGROUND ART

In colonoscopy or bowel surgery, the colon must be preliminarily emptied through bowel cleansing, which involves administration of a bowel-cleansing agent. Hitherto, an electrolyte solution containing polyethylene glycol (PEG electrolyte solution) or diluted magnesium citrate solution (i.e., large volume magnesium citrate method) has been employed as a bowel-cleansing agent. Since PEG electrolyte solution and diluted magnesium citrate solution are liquid agents and have poor flavor, etc., patients encounter difficulty in taking such a liquid agent, which problematically reduces compliance.

In recent years, in order to solve the aforementioned problems, solid bowel-cleansing agents such as tablet-form agents have been developed. The thus-developed solid agents, which are readily taken by subjects, are widely employed in bowel cleansing. Examples of the solid bowel-cleansing agent include a tablet-form agent containing sodium phosphate as an effective ingredient and granules containing as effective ingredients sodium chloride, potassium chloride, sodium bicarbonate, and sodium sulfate. In the case of granules containing a potassium salt, an adverse effect such as hyperpotassemia occurs due to excessive absorption of potassium by a subject, which is problematic. In contrast, since the tablet-form agent contains sodium phosphate as an effective ingredient, the agent causes less adverse effects and is readily taken by a subject, which is advantageous.

In order to reduce the size of the sodium phosphate-containing tablet-form bowel-cleansing agent and ensure moderate dissolution property, crystalline cellulose is incorporated into the agent as an excipient. However, crystalline cellulose often remains in the intestinal tract due to insolubility in water, and the remaining cellulose must be removed through, for example, suction or washing upon colonoscopy, which is problematic.

Meanwhile, it has been reported that polyethylene glycol, which is a water-soluble binder, is added to the sodium phosphate-containing tablet-form bowel-cleansing agent (Patent Document 1). However, dissolution of an ingredient of a tablet containing polyethylene glycol is considerably rapid, which may cause adverse effects. In fact, such an agent has not yet been put on the market in Japan. Furthermore, for fully attaining the binding function of polyethylene glycol, the production thereof preferably includes a heating step. In this case, the water content of raw material must be carefully regulated. In addition, for sufficiently dispersing the binder and uniformly heating polyethylene glycol, the production thereof often requires discontinuous batch treatments.

RELATED ART DOCUMENTS

Patent Documents

[Patent Document 1] JP-A-2007-512336
[Patent Document 2] JP-B-1995-8809
[Patent Document 3] JP-A-1995-258078
[Patent Document 4] JP-A-1998-130142
[Patent Document 5] Japanese Patent No. 2667214
[Patent Document 6] Japanese patent No. 2930875

SUMMARY OF THE INVENTION

Problems to be Solved by the Invention

Thus, an object of the present invention is to provide a peroral tablet for bowel cleansing which leaves no remains in the intestinal tract after bowel cleansing, which exhibits a dissolution property equivalent to that of conventional sodium phosphate-containing tablets including crystalline cellulose, and which is a small-size agent readily taken by a subject.

Means for Solving the Problems

The present inventors previously produced sodium phosphate-containing tablets by use of a water-soluble polymer other than polyethylene glycol, and carried out extensive studies on size reduction, dissolution property, and property of leaving remains in the intestinal tract. As a result, the inventors found that sodium phosphate-containing tablets exhibiting excellent dissolution property can be produced, in some cases, by use of hydroxypropyl cellulose as an excipient.

Hydroxypropyl cellulose is a water-soluble polymer, and is employed as an additive for long-term sustained release preparations. Hitherto, there have been known techniques in which hydroxypropyl cellulose is used singly or in combination with hydroxypropylmethyl cellulose to attain sustained release of a drug of poor solubility (Patent Documents 2 to 4), a technique of attaining sustained release of a basic drug (Patent Document 5), and a technique in which hydroxypropyl cellulose is used in combination with ethyl cellulose to attain sustained release of a drug (Patent Document 6). However, the action of hydroxypropyl cellulose on sodium phosphate, which is water-soluble and per se has excellent dissolution property, has never been elucidated.

The inventors previously produced sodium phosphate-containing tablets by use of hydroxypropyl cellulose, whereby the following was elucidated. Tablets having excellent dissolution property were produced by use of a large amount of hydroxypropyl cellulose. In this case, however, remains were found in the evaluation on residue considering intestinal tract conditions, and the size of tablets increased, thereby making the tablets difficult to take. When a small amount of hydroxypropyl cellulose was added to the tablets, a dissolution property equivalent to that of a conventional tablet-form agent containing crystalline cellulose was not attained.

Then, the present inventors have carried out extensive studies on the ranges in particle size and viscosity of hydroxypropyl cellulose and on the amount thereof for down-sizing the tablets within a range of 15 mass %. As a result, the inventors have found that, even when the sodium phosphate content is ≧80 mass %, a peroral tablet for bowel cleansing which has a dissolution property equivalent to that of a conventional tablet, which contains virtually no water-insoluble ingredient, and which does not remain in the intestinal tract can be produced by use of hydroxypropyl cellulose having a particle size and a viscosity falling within specific ranges. The present invention has been accomplished on the basis of this finding.

Accordingly, the present invention provides a peroral tablet for bowel cleansing comprising the following ingredients (A) and (B):

(A) 80 to 95 mass % of sodium phosphate, and (B) (B1) 7 to 11 mass % of hydroxypropyl cellulose which has such a particle size that ≧99% of the particles thereof pass through a mesh having an opening of 350 μm and whose 2-mass % aqueous solution has a viscosity of 2.0 to 10.0 mPa.s, (B2) 5 to 13 mass % of hydroxypropyl cellulose which has such a particle size that 99% of the particles thereof pass through a mesh having an opening of 150 μm and whose 2-mass % aqueous solution has a viscosity of 3.0 to 5.9 mPa.s, or (B3) 7 to 11 mass % of hydroxypropyl cellulose which has such a particle size that 99% of the particles thereof pass through a mesh having an opening of 150 μm and whose 2-mass % aqueous solution has a viscosity of 6.0 to 4,000 mPa.s, and having a water-insoluble ingredient content of 5 mass % or less.

Effects of the Invention

When the peroral tablet for bowel cleansing of the present invention, which contains a very small amount of a water-insoluble ingredient, is taken by a subject, no insoluble matter remains in the intestinal tract after bowel cleansing. In addition, since the sodium phosphate content of the tablet is 80 mass % or more, small-size tables which are readily taken by a subject can be provided. The sodium phosphate dissolution property of the tablet of the invention is equivalent to that of a tablet prepared with crystalline cellulose and, therefore, no adverse effects occur. Furthermore, since the tablet of the invention can be produced without a heating step, continuous production thereof can be realized. Thus, sodium phosphate does not undergo heat-induced chemical change, thereby producing stable-quality tablets, which is advantageous.

MODES FOR CARRYING OUT THE INVENTION

In the tablet of the present invention, (A) sodium phosphate serves as an effective ingredient of the peroral bowel-cleansing agent. Specific examples of (A) sodium phosphate include sodium dihydrogenphosphate monohydrate and disodium hydrogenphosphate anhydrate. Preferably, sodium dihydrogenphosphate monohydrate and disodium hydrogenphosphate anhydrate are used in combination.

From the viewpoint of size reduction of tablets, the tablet of the present invention preferably contains (A) sodium phosphate in an amount of 80 to 95 mass %, more preferably 90 to 95 mass %. Needless to say, a larger sodium phosphate content is advantageous for attaining size reduction. When the total amount of sodium dihydrogenphosphate monohydrate (A1) and disodium hydrogenphosphate anhydrate (A2) is 100 parts by mass, the A1 content is preferably 70 to 75 parts by mass (more preferably 73.47 parts by mass), and the A2 content is preferably 25 to 30 parts by mass (more preferably 26.53 parts by mass).

The tablet of the present invention contains hydroxypropyl cellulose as an excipient. Only when hydroxypropyl cellulose is incorporated into a tablet in a specific amount according to the particle size and the viscosity of the solution thereof, as described hereinbelow, the produced tablet exhibits a sodium phosphate dissolution property equivalent to that of a conventional tablet containing crystalline cellulose. When the hydroxypropyl cellulose content is 15 mass % or more, the tablet contains the effective ingredient in a reduced amount. In this case, large-size tablets, which are not readily taken by a subject, must be produced. In addition, such tablets leave remains in the intestinal tract after bowel cleansing. In the present invention, viscosity is determined at 20° C. by means of a type B viscometer.

In the case of (B1) hydroxypropyl cellulose which has such a particle size that ≧99% of the particles thereof pass through a mesh having an opening of 350 μm and whose 2-mass % aqueous solution has a viscosity of 2.0 to 10.0 mPa.s, the (B1) content is 7 to 11 mass %, preferably 8 to 10 mass %.

In the case of (B2) hydroxypropyl cellulose which has such a particle size that ≧99% of the particles thereof pass through a mesh having an opening of 150 μm and whose 2-mass % aqueous solution has a viscosity of 3.0 to 5.9 mPa.s, the (B2) content is 5 to 13 mass %, preferably 5 to 10 mass %.

In the case of (B3) hydroxypropyl cellulose which has such a particle size that 99% of the particles thereof pass through a mesh having an opening of 150 μm and whose 2-mass % aqueous solution has a viscosity of 6 to 4,000 mPa.s, the (B3) content is 7 to 11 mass %, preferably 8 to 10 mass %.

When the hydroxypropyl cellulose (B1) has such a particle size that ≧99% of the particles thereof pass through a mesh having an opening of 350 μm but whose 2-mass % aqueous solution has a viscosity in excess of 10.0 mPa.s, a satisfactory dissolution property cannot be attained. When the hydroxypropyl cellulose (B1) has such a particle size that 99% of the particles thereof pass through a mesh having an opening of 350 μm and whose 2-mass % aqueous solution has a viscosity of 2.0 to 10.0 mPa.s, but the (B1) content is less than 7 mass %, a satisfactory dissolution property cannot be attained.

When the hydroxypropyl cellulose (B2) has such a particle size that ≧99% of the particles thereof pass through a mesh having an opening of 150 μm and whose 2-mass % aqueous solution has a viscosity of 3.0 to 5.9 mPa.s, but the (B2) content is less than 5 mass %, a satisfactory dissolution property cannot be attained.

When the hydroxypropyl cellulose (B3) has such a particle size that ≧99% of the particles thereof pass through a mesh having an opening of 150 μm and whose 2-mass % aqueous solution has a viscosity of 6 to 4,000 mPa.s, a satisfactory dissolution property can be attained only in the case where the (B3) content falls within a narrow range of 7 to 11 mass %.

Among the aforementioned hydroxypropyl cellulose species, a hydroxypropyl cellulose falling within the scope of (B2) is preferred. In a particularly preferred mode, the employed hydroxypropyl cellulose has such a particle size that 99% of the particles thereof pass through a mesh having an opening of 150 μl and whose 2-mass % aqueous solution has a viscosity of 3.0 to 5.9 mPa.s, and the hydroxypropyl cellulose content is 5 to 10 mass %. This case is particularly preferred from the viewpoints of dissolution property, residual property in the intestinal tract, and reduction of tablet size.

In the present invention, any hydroxypropyl cellulose species which satisfy the standards of The Japanese Pharmacopoeia Fifteenth Edition may be employed. Those having a particle size and viscosity falling within the aforementioned ranges may be available from, for example, Nippon Soda Co., Ltd.

The tablets of the present invention may further contain 5 mass % or less of water-insoluble ingredients such as magnesium stearate as a lubricant and light anhydrous silicic acid as a fluidizing agent. These insoluble ingredients are preferably incorporated into a tablet for the purpose of facilitating production thereof. In the present invention, insoluble ingredients are preferably incorporated into a tablet in a total amount of 5 mass % or less, more preferably 3 mass % or less, particularly preferably 2 mass % or less, in order not to leave remains in the intestinal tract after bowel cleansing. The lower limit of the water-insoluble ingredient level is preferably 1 mass %.

The mass of the tablet of the present invention is preferably 1.5 g/tablet or less, more preferably 0.9 to 1.5 g/tablet, particularly preferably 1.0 to 1.2 g/tablet, from the viewpoint of easiness of taking thereof.

No particular limitation is imposed on the shape of the tablet of the present invention, so long as the efficacy of the tablet is fully attained. The ratio of the shortest diameter to the longest diameter in a cross-section of the tablet is preferably 0.5 to 1.0, and the ratio of the shortest diameter in a cross-section of the tablet to the thickness of the tablet is preferably 0.5 to 2.0.

No particular limitation is imposed on the particle size of sodium phosphate, so long as the particle size is suitable for production of tablets and such a particle size ensures efficacy of the tablets. However, sodium phosphate may be further pulverized.

The tablet of the present invention may be produced through a routine tablet production process. However, in order to improve the tablet production process, the process may include a granulation step. In the case where an effective ingredient contains water therein, a dry-format granulation step is preferably selected from the viewpoint of control of the water content during tablet production. In a more preferred embodiment of the production, sodium phosphate and hydroxypropyl cellulose are mixed together, and the mixture is pulverized and granulated in a dry format. Magnesium stearate is added to the granulated product before pelletizing, and the mixture is pelletized, whereby the target tablets can be produced. The above granulation step requires no heat treatment and is continuously performed. Thus, small-size tablets can be formed.

EXAMPLES

The present invention will next be described in detail by way of examples.

Example 1

In all the Examples and Comparative Examples, tablets were prepared from sodium dihydrogenphosphate monohydrate (734.7 mg/tablet), disodium hydrogenphosphate anhydrate (265.3 mg/tablet), magnesium stearate (1.5%/tablet), and a predetermined amount of hydroxypropyl cellulose. The particle size of hydroxypropyl cellulose and the viscosity of the solution thereof were changed, to thereby prepare tablets of the Examples and the Comparative Examples shown in Table 1. The tablets were prepared through a pulverizing step, a dry-granulating step, a spherizing step, a mixing step, and a pelletizing step (pelletizing pressure: about 25 kN), in combination.

TABLE 1

| | Particle size | | | | | | |
|---|---|---|---|---|---|---|---|
| | ≧99% Particles (opening of ≦150 μm) | | | ≧99% Particles (opening of ≦350 μm) | | | |
| | Viscosity*[1] | | | | | | |
| Content: | 3.0 to 5.9 | 6.0 to 10.0 | 1000 to 4000 | 2.0 to 2.9 | 3.0 to 5.9 | 6.0 to 10.0 | 1000 to 4000 |
| 4% | Comp. Ex. 1 | | Comp. Ex. 2 | | | | |
| 5% | Ex. 1 | Comp. Ex. 3 | Comp. Ex. 4 | | | Comp. Ex. 5 | Comp. Ex. 6 |
| 7.6% | Ex. 2 | Ex. 3 | Ex. 4 | Ex. 5 | Ex. 6 | Ex. 7 | |
| 10% | Ex. 8 | Ex. 9 | Ex. 10 | Ex. 11 | Ex. 12 | Ex. 13 | Comp. Ex. 7 |
| 12% | Ex. 14 | | | | | | |
| 15% | Comp. Ex. 8 | Comp. Ex. 9 | | | Comp. Ex. 10 | Comp. Ex. 11 | |
| 20% | | | Comp. Ex. 12 | Comp. Ex. 13 | | Comp. Ex. 14 | Comp. Ex. 15 |

*[1]Viscosity (mPa·s): viscosity of 2% hydroxypropyl cellulose solution at 20° C.

The aforementioned tablet preparation procedure was repeated, except that the dry-granulating step was changed to a wet-granulating step, to thereby prepare tablets of Examples and Comparative Example shown in Table 2. Tablets of Examples 17 were prepared through fluidized bed granulation, and agitation granulation was employed in the other Examples and Comparative Examples.

TABLE 2

| | Particle size | | | | | | |
|---|---|---|---|---|---|---|---|
| | ≧99% Particles (opening of ≦150 μm) | | | ≧99% Particles (opening of ≦350 μm) | | | |
| | Viscosity*¹ | | | | | | |
| Content: | 3.0 to 5.9 | 6.0 to 10.0 | 1000 to 4000 | 2.0 to 2.9 | 3.0 to 5.9 | 6.0 to 10.0 | 1000 to 4000 |
| 10% | Ex. 15 | Ex. 16<br>Ex. 17*² | Ex. 18 | | | Ex. 19 | Comp. Ex. 16 |

*¹Viscosity (mPa · s): viscosity of 2% hydroxypropyl cellulose solution at 20° C.
*²Prepared through fluidized bed granulation, and agitation granulation was employed in the other Examples and Comparative Examples.

Comparative Example 17

Visiclear (Registered trademark) Tablets (product of Zeria Pharmaceutical Co., Ltd.)
<Evaluation of Dissolution Property>
Tablets of Examples 1 to 14 and those of Comparative Examples 1 to 15

Dissolution properties of Visiclear (Registered trademark) Tablets and those of the tablets of the Examples and Comparative Examples were determined through the dissolution test as stipulated in The Japanese Pharmacopoeia (the paddle method; test liquid: water, paddle rotation: 50 rpm). The dissolution property of each tablet was evaluated according to "Guidelines on production and sales of drugs, guidelines on bioequivalence test of generic drugs, determination of similarity in dissolution behavior (Chapter 3. V: 4. Dissolution test)." When similarity in dissolution property to Visiclear Tablets was found, the tablets are marked with "A," whereas when no similarity was found, the tablets are marked with "B." The results are shown in Table 3. Among the tablets having a low hydroxypropyl cellulose content (Example 1, and Comparative Examples 1 to 6), similarity was found only in tablets of Example 1. When the hydroxypropyl cellulose content was 7.6 to 10.0% (Examples 2 to 13, and Comparative Example 7), among six hydroxypropyl cellulose species having different particle sizes or solution viscosities, similarity was found in tablets of the Examples other than the case where hydroxypropyl cellulose has such a particle size that ≧99% of the particles thereof pass through a mesh having an opening of 350 μm and has a solution viscosity of 1,000 to 4,000 mPa.s. When the hydroxypropyl cellulose content was increased further, similarity was found in tablets of all formulations (Example 14, and Comparative Examples 8 to 15). In other words, addition of hydroxypropyl cellulose in a certain amount was required in order to attain similarity in dissolution property. When a hydroxypropyl cellulose having a large particle size and a high solution viscosity was employed, the amount of hydroxypropyl cellulose to be added increased. In contrast, through employment of a hydroxypropyl cellulose having a small particle size and a low solution viscosity, similarity in dissolution property could be ensured by a smaller amount hydroxypropyl cellulose.

TABLE 3

| | Particle size | | | | | | |
|---|---|---|---|---|---|---|---|
| | ≧99% Particles (opening of ≦150 μm) | | | ≧99% Particles (opening of ≦350 μm) | | | |
| | Viscosity*¹ | | | | | | |
| Content: | 3.0 to 5.9 | 6.0 to 10.0 | 1000 to 4000 | 2.0 to 2.9 | 3.0 to 5.9 | 6.0 to 10.0 | 1000 to 4000 |
| 4% | Comp. Ex. 1<br>B | | Comp. Ex. 2<br>B | | | | |
| 5% | Ex. 1<br>A | Comp. Ex. 3<br>B | Comp. Ex. 4<br>B | | | Comp. Ex. 5<br>B | Comp. Ex. 6<br>B |
| 7.6% | Ex. 2<br>A | Ex. 3<br>A | Ex. 4<br>A | Ex. 5<br>A | Ex. 6<br>A | Ex. 7<br>A | |
| 10% | Ex. 8<br>A | Ex. 9<br>A | Ex. 10<br>A | Ex. 11<br>A | Ex. 12<br>A | Ex. 13<br>A | Comp. Ex. 7<br>B |
| 12% | Ex. 14<br>A | | | | | | |
| 15% | Comp. Ex. 8<br>A | Comp. Ex. 9<br>A | | | Comp. Ex. 10<br>A | Comp. Ex. 11<br>A | |
| 20% | | | Comp. Ex. 12<br>B | Comp. Ex. 13<br>A | | Comp. Ex. 14<br>A | Comp. Ex. 15<br>A |

*¹Viscosity (mPa · s): viscosity of 2% hydroxypropyl cellulose solution at 20° C.

<Evaluation of Similarity in Dissolution Property>
Tablets of Examples 15 to 19 and Those of Comparative Example 16

Dissolution property evaluation was carried out in a manner similar to that of evaluation carried out on the tablets of Examples 1 to 14 and those of Comparative Examples 1 to 15. Table 4 shows the results. The results were similar to those of Examples 8 to 13 and Comparative Example 7. Thus, dissolution properties were found to be unvaried by the employed granulating method. However, sodium dihydrogenphosphate and disodium hydrogenphosphate anhydrate employed in the Examples may be dehydrated or absorb water during tablet production. Therefore, the tablets are preferably produced through the dry-granulating method or the direct pelletizing method.

Example 9), the residue level became worse with increasing content of hydroxypropyl cellulose. Thus, the level "±" was employed as a threshold of an acceptable range, and evaluation of worse cases was omitted in some cases. In addition, tablets having a hydroxypropyl cellulose content lower than a corresponding threshold should exhibit an improved residue

TABLE 4

| | Particle size | | | | | | |
|---|---|---|---|---|---|---|---|
| | ≧99% Particles (opening of ≦150 μm) | | | ≧99% Particles (opening of ≦350 μm) | | | |
| | | | Viscosity*[1] | | | | |
| Content: | 3.0 to 5.9 | 6.0 to 10.0 | 1000 to 4000 | 2.0 to 2.9 | 3.0 to 5.9 | 6.0 to 10.0 | 1000 to 4000 |
| 10% | Ex. 15 A | Ex. 16 A Ex. 17 A*[2] | Ex. 18 A | | | Ex. 19 A | Comp. Ex. 16 B |

*[1]Viscosity (mPa · s): viscosity of 2% hydroxypropyl cellulose solution at 20° C.
*[2]Prepared through fluidized bed granulation, and agitation granulation was employed in the other Examples and Comparative Examples.

<Evaluation on Residue>

Most ingredients of the tablets of the Examples and Comparative Examples are water-soluble (excepting Comparative Example 17). However, unless a tablet disappears within a specific period of time, the target endoscopic examination is disturbed and fails to be completed. Thus, four hours after start of the dissolution test, test subjects (n=3) were visually observed or examined by hand. In the case where three test subjects exhibit "absence of drug residue" or "presence of muddy matter," a rating of "−" is given. In the case where one or two test subjects exhibit "absence of drug residue" or "presence of muddy matter," a rating of "±" is given. In the case where three test subjects exhibit "presence of drug residue" or "muddy matter having central core," a rating of "+" is given. Evaluation of residue was performed on the tablets of the Examples and Comparative Examples which exhibited similarity in dissolution property. The results and the residue evaluation results of Comparative Example 17 (Visiclear (Registered trademark) Tablets) are shown in Table 5 (as for Comparative Example 17, see the footnote below). As shown in the scores of Examples 8 and 14 and Comparative Example 8 (similarly in those of Examples 3 and 9 and Comparative score. Thus, evaluation of such cases was omitted. Notably, Visiclear (Registered trademark) Tablets (Comparative Example 17) was rated with "+." Therefore, residue scores of the Examples rated with "−" and "±" are considered to indicate clear improvement.

TABLE 5

| | Particle size | | | | | | |
|---|---|---|---|---|---|---|---|
| | ≧99% Particles (opening of ≦150 μm) | | | ≧99% Particles (opening of ≦350 μm) | | | |
| | | | Viscosity*[1] | | | | |
| Content: | 3.0 to 5.9 | 6.0 to 10.0 | 1000 to 4000 | 2.0 to 2.9 | 3.0 to 5.9 | 6.0 to 10.0 | 1000 to 4000 |
| 4% | | | | | | | |
| 5% | | | | | | | |
| 7.6% | Ex. 2 − | Ex. 3 − | | | | | |
| 10% | Ex. 8 − | Ex. 9 ± | Ex. 10 ± | Ex. 11 ± | Ex. 12 ± | Ex. 13 ± | |
| 12% | Ex. 14 ± | | | | | | |
| 15% | Comp. Ex. 8 + | Comp. Ex. 9 + | | | | | |
| 20% | | | | | | | |

*[1]Viscosity (mPa · s): viscosity of 2% hydroxypropyl cellulose solution at 20° C.
Comp. Ex. 17 (Visiclear (Registered trademark) Tablets): "+"

<Purgative Action Tested in Dogs>

Each test tablet preparation was perorally administered with a predetermined amount of distilled water to dogs, and the time required for the first excretion of colorless feces was measured.

Test animals: male dogs (beagles), 7-month-old
Test preparations: Examples 1 and 8 and Comparative Example 17 (Visiclear (Registered trademark) Tablets)
Method of Administration:

After fasting of 18 hours, each test preparation (1.5 tablets (1.5 g as phosphate)) and water (100 mL) were administered to respective dogs. The administration was repeated 10 times in total with intervals of 15 minutes (15 tablets and 1,000 mL of water in total).

Measurement:

The period of time from start of the administration to the point in time when colorless feces were observed at the first time was measured.

TABLE 6

| | Results | | |
|---|---|---|---|
| Drug preparation | Time (min) | S.D. (min) | No. of animals |
| Ex. 1 | 109 | 14 | 4 |
| Ex. 8 | 161 | 40 | 4 |
| Comp. Ex. 17 | 138 | 28 | 4 |

Under the direction/dose conditions "start taking in a tablet(s) 4 to 6 hours before the colon examination" described in the package insert of Visiclear (Registered trademark) Tablets (Comparative Example 17), tablets of Examples 1 and 8 exhibited a satisfactory bowel cleansing effect.

The invention claimed is:

1. A method for bowel cleansing, comprising administering to a patient in need thereof a peroral tablet comprising:
   (A) 80 to 95 mass % of sodium phosphate, wherein the sodium phosphate (A) comprises sodium dihydrogenphosphate monohydrate and disodium hydrogenphosphate anhydrate, and wherein a content of sodium dihydrogenphosphate monohydrate is 70 to 75 parts by mass and a content of disodium hydrogenphosphate anhydrate is 25 to 30 parts by mass when a total amount of sodium dihydrogenphosphate monohydrate and disodium hydrogenphosphate anhydrate is 100 parts by mass; and
   (B) a cellulose comprising at least one selected from the group consisting of
   (B1) 7 to 11 mass % of a hydroxypropyl cellulose having particle sizes such that >99% of particles thereof pass through a mesh having an opening of 350 gm and whose 2-mass % aqueous solution has a viscosity of 2.0 to 10.0 mPa.s,
   (B2) 5 to 13 mass % of a hydroxypropyl cellulose having particle sizes such that >99% of the particles thereof pass through a mesh having an opening of 150 gm and whose 2-mass % aqueous solution has a viscosity of 3.0 to 5.9 mPa.s, and
   (B3) 7 to 11 mass % of a hydroxypropyl cellulose having particle sizes such that >99% of the particles thereof pass through a mesh having an opening of 150 jam and whose 2-mass % aqueous solution has a viscosity of 6.0 to 4,000 mPa.s,
   wherein the peroral tablet has a water insoluble ingredient content of 5 mass % or less.

2. The method of claim 1, wherein the content of the sodium phosphate (A) is 90 to 95 mass %.

3. The method of claim 1, wherein the peroral tablet comprises the hydroxypropyl cellulose (B2).

4. The method of claim 3, wherein a content of the hydroxypropyl cellulose (B2) is 5 to 10 mass %.

5. The method of claim 1, wherein the water-insoluble ingredient content is 3 mass % or less.

6. The method of claim 1, wherein the water-insoluble ingredient content is 2 mass % or less.

7. The method of claim 1, wherein the water-insoluble ingredient content is 1 mass % or less.

8. The method of claim 1, wherein the peroral tablet comprises the hydroxypropyl cellulose (B1).

9. The method of claim 1, wherein the peroral tablet comprises the hydroxypropyl cellulose (B3).

* * * * *

UNITED STATES PATENT AND TRADEMARK OFFICE
CERTIFICATE OF CORRECTION

PATENT NO. : 8,454,995 B2  
APPLICATION NO. : 13/392605  
DATED : June 4, 2013  
INVENTOR(S) : Masafumi Nomura et al.

Page 1 of 1

It is certified that error appears in the above-identified patent and that said Letters Patent is hereby corrected as shown below:

In the Claims

Claim 1, Column 11, line 32, "particle sizes such that >99% of particles thereof pass"  
should read --particle sizes such that ≥99% of particles thereof pass--

Claim 1, Column 12, line 1, "through a mesh having an opening of 350 gm and"  
should read --through a mesh having an opening of 350 μm--

Claim 1, Column 12, line 3, "2.0 to 10.0 mPa.s,"  
should read --2.0 to 10.0 mPa·s--

Claim 1, Column 12, line 5, "particle sizes such that >99% of the particles thereof"  
should read --particle sizes such that ≥99% of the particles thereof--

Claim 1, Column 12, line 6, "pass through a mesh having an opening of 150 gm and"  
should read --pass through a mesh having an opening of 150 μm and--

Claim 1, Column 12, line 8, "3.0 to 5.9 mPa.s, and"  
should read --3.0 to 5.9 mPa·s, and--

Signed and Sealed this  
Twenty-third Day of July, 2013

Teresa Stanek Rea  
*Acting Director of the United States Patent and Trademark Office*

UNITED STATES PATENT AND TRADEMARK OFFICE
CERTIFICATE OF CORRECTION

| | | Page 1 of 1 |
|---|---|---|
| PATENT NO. | : 8,454,995 B2 | |
| APPLICATION NO. | : 13/392605 | |
| DATED | : June 4, 2013 | |
| INVENTOR(S) | : Masafumi Nomura et al. | |

It is certified that error appears in the above-identified patent and that said Letters Patent is hereby corrected as shown below:

In the Claims

Column 12, line 10, "particle sizes such that >99% of the particles thereof"
should read --particle sizes such that ≥99% of the particles thereof--

Column 12, line 11, "pass through a mesh having an opening of 150 jam"
should read --pass through a mesh having an opening of 150 μm--

Column 12, line 13, "of 6.0 to 4,000 mPa.s,"
should read --of 6.0 to 4,000 mPa·s,--

Signed and Sealed this
Twenty-seventh Day of January, 2015

Michelle K. Lee
*Deputy Director of the United States Patent and Trademark Office*